United States Patent
Zorman et al.

(10) Patent No.: US 10,772,545 B2
(45) Date of Patent: Sep. 15, 2020

(54) NON-INVASIVE METHOD FOR MEASURING A PHYSIOLOGICAL PARAMETER VIA A CONFOCAL SPECTROSCOPIC MEASUREMENT DEVICE

(71) Applicant: Bioserenity, Paris (FR)

(72) Inventors: Sylvain Zorman, Paris (FR); Pierre-Yves Frouin, Paris (FR)

(73) Assignee: Bioserenity (FR)

( * ) Notice: Subject to any disclaimer, the term of this patent is extended or adjusted under 35 U.S.C. 154(b) by 273 days.

(21) Appl. No.: 15/550,902

(22) PCT Filed: Feb. 15, 2016

(86) PCT No.: PCT/EP2016/053151
§ 371 (c)(1),
(2) Date: Aug. 14, 2017

(87) PCT Pub. No.: WO2016/131763
PCT Pub. Date: Aug. 25, 2016

(65) Prior Publication Data
US 2018/0042536 A1   Feb. 15, 2018

(30) Foreign Application Priority Data

Feb. 17, 2015   (FR) ...................................... 15 51336

(51) Int. Cl.
*A61B 5/1455*   (2006.01)
*A61B 5/00*   (2006.01)
*A61B 5/01*   (2006.01)

(52) U.S. Cl.
CPC ........ *A61B 5/14552* (2013.01); *A61B 5/0068* (2013.01); *A61B 5/0075* (2013.01);
(Continued)

(58) Field of Classification Search
None
See application file for complete search history.

(56) References Cited

U.S. PATENT DOCUMENTS 5,353,790 A   10/1994  Jacques et al.
5,632,272 A *  5/1997  Diab .................... G06K 9/0051
                                                    600/323
(Continued)

FOREIGN PATENT DOCUMENTS

GB        2307295 A     5/1997
WO     2010075385 A2    7/2010
(Continued)

OTHER PUBLICATIONS

International Search Report for Application No. PCT/EP2016/053151 dated May 11, 2016.
(Continued)

*Primary Examiner* — Eric F Winakur
*Assistant Examiner* — Marjan Fardanesh
(74) *Attorney, Agent, or Firm* — Lerner, David, Littenberg, Krumholz & Mentlik, LLP

(57) ABSTRACT

The present invention relates to a method for measuring a physiological parameter of a subject by means of an optical measurement device, said method comprising the steps of:

setting into place the optical measurement device (1, 1bis) facing a skin surface (10) of the subject, so that the object focal spot of the optical objective is positioned at a predetermined skin depth, receiving by the photosensitive receiver (4) light rays from the first object focal spot, at the predetermined skin depth, analyzing the light rays received by the photosensitive receiver (4), and comparing the results of the analysis with known data, so as to determine the physiological parameter of the subject.

2 Claims, 2 Drawing Sheets

(52) U.S. Cl.
CPC ............... *A61B 5/01* (2013.01); *A61B 5/441* (2013.01); *A61B 5/443* (2013.01); *A61B 2562/0242* (2013.01)

(56) References Cited

U.S. PATENT DOCUMENTS

| | | | | |
|---|---|---|---|---|
| 6,088,087 | A * | 7/2000 | Graves | A61B 5/0059 356/39 |
| 6,358,216 | B1 * | 3/2002 | Kraus | A61B 5/6844 374/E13.003 |
| 8,462,356 | B2 * | 6/2013 | Wadman | A61B 5/0059 348/208.12 |
| 2006/0063993 | A1 | 3/2006 | Yu et al. | |

FOREIGN PATENT DOCUMENTS

| | | |
|---|---|---|
| WO | 2011151744 A1 | 12/2011 |
| WO | 2014006827 A1 | 1/2014 |

OTHER PUBLICATIONS

French Preliminary Search Report for Application No. FR1551336 dated Dec. 9, 2015.

Meglinskii et al., "Study of the possiblity of increasing the probing depth by the method of reflection confocal microscopy upon immersion clearing of near-surface human skin layers", Quantum Electronics, Turpion Ltd., London, GB, vol. 32, No. 10, Oct. 1, 2002, pp. 875-882.

* cited by examiner

NON-INVASIVE METHOD FOR MEASURING A PHYSIOLOGICAL PARAMETER VIA A CONFOCAL SPECTROSCOPIC MEASUREMENT DEVICE

CROSS REFERENCE TO RELATED APPLICATIONS

The present application is a national phase entry under 35 U.S.C. § 371 of International Application No. PCT/EP2016/053151 filed Feb. 15, 2016, published in French, which claims priority from French Patent Application No. 1551336 filed Feb. 17, 2015, the disclosures of which are incorporated herein by reference.

FIELD OF THE INVENTION

The present invention relates to methods for measuring a physiological parameter of a subject.

STATE OF THE ART

Spectroscopy is a non-invasive method allowing study, analysis or quantification of a physico-chemical parameter. This type of approach applied to human physiology, allows the measurement in a non-invasive way of vital parameters such as temperature, heart rate, oxygen saturation level in the blood or bilirubin level.

The spectroscopy is applied by a sensor positioned close to the skin which measures the optical properties of the surface layers of the skin.

A significant limitation of the measurement of physiological parameters by spectroscopy is that the heterogeneity of the surface layers of the skin induces perturbations which degrade the measurement.

Several strategies have been proposed for limiting the presence of parasitic radiations from the layers of the skin adjacent to the layer of the skin of interest. Mention may be made of the use of polarized light combined with a detector positioned at the Brewster angle as described in document WO2011151744 A1, the use of numerical correction factors, as described in document U.S. Pat. No. 5,353,790 A, or further the use of optical fibers oriented and positioned so as to be coupled to different skin depths, as described in patent WO2014006827 A1.

DISCUSSION OF THE INVENTION

An object of the invention is to propose a method for measuring a physiological parameter of a subject by means of an optical measurement device, having improved accuracy.

This object is achieved, within the scope of the present invention, by a method for determining a physiological parameter of a subject which may be applied by means of an optical measurement device comprising:

an optical axis on which is laid out an optical objective comprising a first object focal spot and a second image focal spot, a first plane comprising a pinhole centered on the first image focal spot of the optical objective so as to only let through light rays from the first object focal spot of the optical objective, a photosensitive receiver intended to receive the light rays from the first image focal spot, downstream from the pinhole, a control unit configured for analyzing the light rays received by the photosensitive receiver, and comparing the results of the analysis with known data, said method comprising the steps of:

setting into place the optical measurement device facing a skin surface of the subject, so that the first object focal spot of the optical objective is positioned at a predetermined skin depth, receiving by the photosensitive receiver light rays from the first object focal spot, at the predetermined skin depth, analyzing the light rays received by the photosensitive receiver, and determining said physiological parameter of the subject from characteristics of the received light rays.

The invention is advantageously completed with the following features, taken individually or in any of their technically possible combinations.

The physiological parameter to be determined is the body temperature of a subject.

The light rays having an infrared wavelength comprised between 700 nm and 1 mm are analyzed.

The predetermined skin depth is comprised in the dermis or hypodermis, preferably between 100 µm and 1.5 mm in depth.

the optical objective comprises a second object focal spot and a second image focal spot, the second image focal spot coinciding with the first object focal spot, the measurement device further comprises:

at least one light source, a second plane comprising a pinhole centered on the second object focal spot so as to only let through the light rays emitted by the light source from the second object focal spot, a semi-reflective planar mirror, said mirror being configured for transmitting the light rays emitted by the light source towards the optical objective, and for transmitting the light rays from the first object focal spot towards the photosensitive detector.

Said method further comprises the steps of:

emitting light rays by the light source towards the second image focal spot, at the predetermined skin depth, receiving the light rays emitted by the light source, reflected by the skin and coming from the first object focal spot, at the predetermined skin depth, by the photosensitive receiver, measuring the skin absorption level of light rays emitted by the light source(s) from the analysis of the light rays received by the photosensitive receiver, and determining the physiological parameter of the subject from the measured absorption level.

The physiological parameter to be determined is the skin bilirubin level.

The light rays emitted by the light source(s) have a wavelength comprised between 400 and 800 nm.

The predetermined skin depth is comprised in the hypodermis and is preferably greater than 1 mm.

The physiological parameter to be determined is the oxygen and carbon monoxide saturation blood level.

The device comprises two light sources, each emitting light rays with different wavelengths, a first one comprised between 620 and 680 nm and a second one comprised between 780 nm and 1 mm.

The predetermined skin depth is comprised in the dermis or hypodermis, and is preferably greater than 0.2 mm.

DESCRIPTION OF THE FIGURES

Other objects, characteristics and advantages will become apparent from the detailed description which follows with reference to the given drawings as an illustration and not as a limitation wherein.

DETAILED DESCRIPTION OF THE INVENTION

Figure 1:
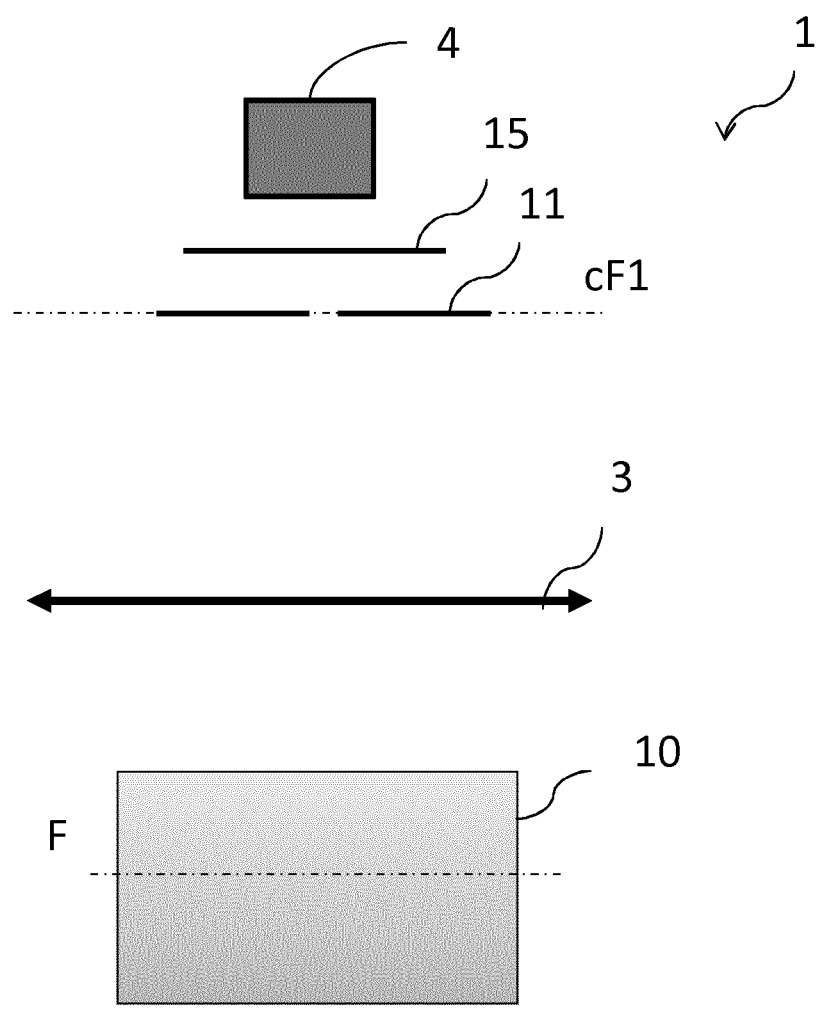
FIG. 1 represents a device for applying a method according to a first embodiment of the invention.

The method for measuring a physiological parameter of a subject according to a first embodiment of the invention is applied by means of an optical measurement device 1 comprising:

- a photosensitive receiver 4 intended to receive the light rays from the first image focal spot, downstream from a first pinhole 11,
- a suitable objective 3 for focusing the radiations emitted by the biological tissue 10 on the detector 4,
- a first pinhole 11 positioned in a first confocal plane cF1 which is the conjugate by the objective 3 of the focal plane F containing the tissue to be studied.

The objective 3 is typically a lens. The objective 3 conjugates the plane F containing the tissue to be studied with the confocal plane cF1 in which is placed the first pinhole 11. In other words, the first pinhole 11 is centered on the first image focal spot of the optical objective 3 so as to only let through light rays from the first object focal spot of the optical objective, which corresponds to the plane F containing the tissue to be studied. Thus, only the photons from the focal plane F pass through the pinhole 11 and participate in the spectroscopic measurement. The light from planes adjacent to F is blocked by the edges of the hole. The optical measurement device 1 therefore allows selection of the depth of the layer measured spectroscopically.

The optical measurement device 1 advantageously includes a filter 15 positioned between the photosensitive receiver 4 and the first pinhole 11, said filter 15 being adapted so as to only let through the radiations belonging to the frequency band to be analyzed.

The optical measurement device 1 further comprises a control unit configured for analysing the light rays received by the photosensitive receiver 4, and comparing the results of the analysis with known data.

The method comprises the steps of:

setting into place the optical measurement device 1 facing a skin surface 10 of the subject, so that the first object focal spot of the optical objective 3 is positioned at a predetermined skin depth, receiving with the photosensitive receiver 4, light rays from the first object focal spot at the predetermined skin depth, analyzing the light rays received by the photosensitive receiver 4, and comparing the results of the analysis with known data, so as to determine the physiological parameter of interest of the subject.

In a particular embodiment, the physiological parameter to be determined is the body temperature of the subject. The body temperature of the subject is determined by analyzing the intensity of the light radiation having an infrared wavelength comprised between 700 nm and 1 mm emitted by the skin. The photosensitive receiver 4 is adapted for detecting light rays having an infrared wavelength comprised between 700 nm and 1 mm. The predetermined skin depth is comprised in the dermis or hypodermis, preferably between 100 μm and 1.5 mm from the skin surface 10. More preferentially, the predetermined skin depth is greater than 0.5 mm from the skin surface 10.

Figure 2:
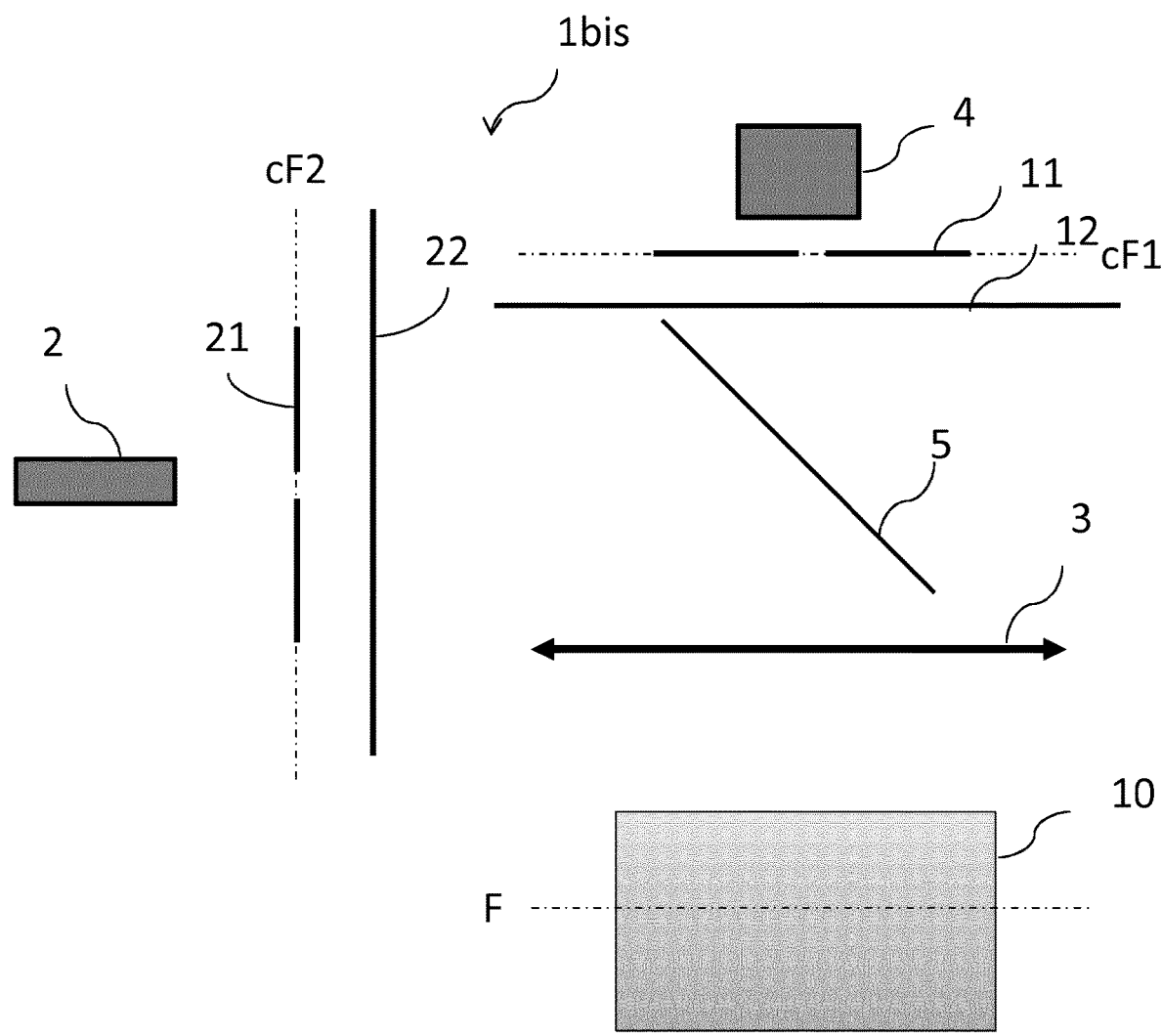
FIG. 2 illustrates a device for applying a method according to a second embodiment of the invention.

In a second embodiment, the method according to claim 1 is applied by a measurement device 1bis, as illustrated by FIG. 2.

The measurement device 1bis includes, in addition to the photosensitive receiver 4, the objective 3, the first pinhole 11 and the control unit described earlier:

- at least one light source 2, typically one or several lasers or diodes,
- a semi-reflective mirror 5 positioned between the detector 4 and the tissue to be studied,
- a second pinhole 21 positioned in a second confocal plane cF2 which is the conjugate, through the objective 3 and the semi-reflective mirror 4, of the focal plane F containing the tissue to be analyzed.

The optical objective 3 comprises a second object focal spot and a second image focal spot, the second image focal spot coinciding with the first object focal spot.

The second pinhole 21 is centered on the second object focal spot so as to only let through the light rays emitted by the light source(s) from the second object focal spot.

It will be understood that in this way, the illumination is concentrated on the focal plane F.

The semi-reflective planar mirror 5 is configured for transmitting the light rays emitted by the light source towards the optical objective, and for transmitting the light rays from the first object focal spot towards the photosensitive detector 4.

Thus, only the photons from the focal plane F pass through the pinhole 11 and participate in the spectroscopic measurement. The light from the adjacent planes (blurred) is blocked by the edges of the hole. It is thus possible to obtain a sharp optical section exclusively corresponding to the focal plane. There is therefore selection of the depth of the layer measured spectroscopically.

The measurement device 1bis may further include a first polarizing plate 12 positioned between the first pinhole 11 and the semi-reflective mirror 5 and a second polarizing plate 22 between the second pinhole 21 and the semi-reflective mirror 5. The polarization axes of both plates 12 and 22 are perpendicular so that the photons from the light source 2 and from the reflection at the surface of the skin 10 do not reach the detector 4. Indeed, as the reflection does not modify the polarization, these photons polarized by the polarizing plate 22 will be absorbed by the polarizing plate 12. Conversely, the photons absorbed and re-emitted in the plane F by the photoactive molecules of the skin 10, have their polarization modified and may cross the polarizing plate F.

The method further comprises the steps of:

emitting light rays by the light source 2 towards the second image focal spot, at the predetermined skin depth, receiving the light rays emitted by the light source(s), reflected by the skin and from the first object focal spot, at the predetermined skin thickness, by the photosensitive receiver 4, determining the level of absorption by the skin of the light rays emitted by the light source from the analysis of the light rays received by the photosensitive receiver 4, and comparing the determined absorption level with known data, so as to determine the physiological parameter of the subject.

Indeed it will be understood that insofar that the emission and reception of the light rays towards/from the focal plane F corresponding to the predetermined skin depth are controlled, it is possible to determine the absorption level by the skin by comparing the rays emitted by the light source(s) via the second pinhole 21 towards the focal plane F and the rays emitted from the focal plane F towards the receiver 4 via the first pinhole 11.

In a particular embodiment, the physiological parameter to be determined is the bilirubin skin level. In this case, the device 1bis comprises at least three sources of light each emitting radiations with different wavelengths comprised between 400 and 800 nm. The emitted wavelengths are also specific to the identification of the dopa-melanin of the red corpuscles and of bilirubin. Preferably, the device 1bis comprises from three to seven light sources. The predetermined skin depth is comprised in this case in the dermis or in the hypodermis and is greater than 0.2 mm.

In another particular embodiment, the physiological parameter to be determined is the oxygen and carbon monoxide saturation blood level. In this case, the device 1bis comprises two light sources 2 each emitting radiations in various wavelengths, a first one comprised between 620 and 680 nm (red) and a second one comprised between 780 and 1 mm (infrared). The predetermined skin depth is comprised in this case at the hypodermis and is greater than 1 mm.

It will be understood that the method for measuring a physiological parameter of a subject as described earlier is particularly advantageous in so far that it allows by means of the objective 3 and of the pinhole(s) 11 and 21 only receiving the light rays from the focal plane F placed at the desired skin depth, consequently reducing considerably the measurement inaccuracies which may be induced by parasitic light radiations.

The invention claimed is:

1. A method for measuring the skin bilirubin level of a subject which is applied by an optical measurement device comprising:
   an optical objective positioned at an optical axis,
   at least three sources of light each emitting radiations with different wavelengths comprised between 400 and 800 nm,
   a first pinhole positioned on a first plane and centered on a first image focal spot of the optical objective so as to only let through light rays from a first object focal spot of the optical objective,
   a second pinhole positioned on a second plane and centered on a second object focal spot of the optical objective so as to let through light rays emitted by the at least three light sources from only the second object focal spot,
   a photosensitive receiver adapted to receive the light rays from the first image focal spot downstream from the first pinhole,
   a semi-reflective planar mirror, said mirror being configured for transmitting the light rays emitted by the at least three light sources towards the optical objective, and for transmitting the light rays from the first object focal spot towards the photosensitive receiver,
   a first polarizing plate positioned between the first pinhole and the semi-reflective mirror and a second polarizing plate positioned between the second pinhole and the semi-reflective mirror, wherein polarization axes of the first polarizing plate and the second polarizing plate are perpendicular,
   said method comprising the steps of:
      setting into place the optical measurement device facing a skin surface of the subject, so that the first object focal spot of the optical objective is positioned at a predetermined skin depth,
      emitting light rays by the at least three light sources towards a second image focal spot of the optical objective, at the predetermined skin depth,
      receiving by the photosensitive receiver light rays emitted by the at least three light sources, reflected by the skin and from the first object focal spot, at the predetermined skin depth,
      measuring an absorption level by the skin of the light rays emitted by the at least three light sources from an analysis of the light rays received by the photosensitive receiver, and
      determining said skin bilirubin level of the subject from comparing the measured absorption level with known data.

2. The method according to claim 1, wherein the predetermined skin depth is greater than 1 mm.

\* \* \* \* \*